United States Patent [19]

Kristiansen et al.

[11] 4,316,908
[45] Feb. 23, 1982

[54] PESTICIDAL SULFINYLAMIDES

[75] Inventors: Odd Kristiansen, Möhlin; Jozef Drabek, Oberwil, both of Switzerland

[73] Assignee: Ciba-Geigy Corporation, Ardsley, N.Y.

[21] Appl. No.: 200,804

[22] Filed: Oct. 27, 1980

[30] Foreign Application Priority Data

Nov. 5, 1979 [CH] Switzerland .......................... 9909/79
Sep. 9, 1980 [CH] Switzerland .......................... 6761/80

[51] Int. Cl.³ .................... A01N 43/28; A01N 43/30; A01N 41/02; C07D 317/12; C07D 339/06; C07C 125/067
[52] U.S. Cl. .................................. 424/277; 424/278; 424/300; 260/340.9 R; 549/39; 560/135; 560/136; 560/137
[58] Field of Search ................... 560/137, 135, 136; 549/39; 260/340.9 R; 424/277, 278, 300

[56] References Cited

U.S. PATENT DOCUMENTS 3,812,174 5/1974 Brown ................................. 560/137
3,950,374 4/1976 Ueda .................................. 560/137

*Primary Examiner*—Natalie Trousof
*Assistant Examiner*—Frederick Pepper

*Attorney, Agent, or Firm*—Frederick H. Rabin

[57] ABSTRACT

Sulfinylamides of the formula

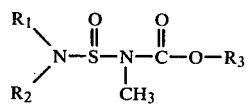

wherein
$R_1$ is hydrogen or $C_1$–$C_6$-alkyl,
$R_2$ is $C_1$–$C_6$-alkyl or $C_1$–$C_6$-alkoxy, and
$R_3$ is phenyl which is unsubstituted or mono- or polysubstituted by identical or different substituents selected from the group comprising halogen, $C_1$–$C_6$-alkyl, $C_1$–$C_6$-alkoxy, $C_1$–$C_6$-alkylthio, $C_2$–$C_6$-alkenyl, $C_2$–$C_6$-alkynyl, nitro,

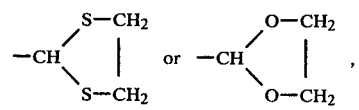

processes for producing them, and their use in combating insect pests.

6 Claims, No Drawings

PESTICIDAL SULFINYLAMIDES

The present invention relates to sulfinylamides, to processes for producing them, and to their use for combating insect pests.

The sulfinylamides have the formula

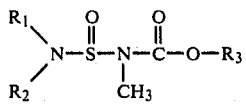

wherein
$R_1$ is hydrogen or $C_1$-$C_6$-alkyl,
$R_2$ is $C_1$-$C_6$-alkyl or $C_1$-$C_6$-alkoxy, and
$R_3$ is phenyl which is unsubstituted or mono- or polysubstituted by identical or different substituents selected from the group comprising halogen, $C_1$-$C_6$-alkyl, $C_1$-$C_6$-alkoxy, $C_1$-$C_6$-alkylthio, $C_2$-$C_6$-alkenyl, $C_2$-$C_6$-alkynyl, nitro,

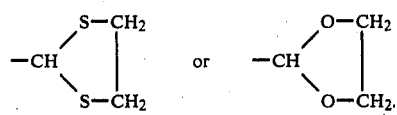

Halogen in the case of $R_3$ is fluorine, chlorine, bromine and iodine, particularly however chlorine and bromine.

The alkyl, alkoxy, thioalkyl, alkenyl and alkynyl groups denoted by $R_1$, $R_2$ and $R_3$ can be straight-chain or branched-chain. Examples of groups of this type are, inter alia: methyl, methoxy, methylthio, ethyl, ethoxy, ethylthio, n-propyl, n-propoxy, n-propylthio, isopropyl, isopropoxy, isopropylthio, n-, i-, sec- or tert-butyl, n-pentyl, n-hexyl and isomers thereof, allyl and propargyl.

Compounds of the formula I which are of importance on account of their action are those wherein
$R_1$ is methyl,
$R_2$ is methyl or methoxy, and
$R_3$ is phenyl which is mono- to trisubstituted by $C_1$-$C_6$-alkyl, $C_1$-$C_6$-alkoxy, $C_1$-$C_6$-alkylthio or

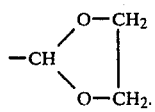

Of particular importance are the following compounds of the formula I:

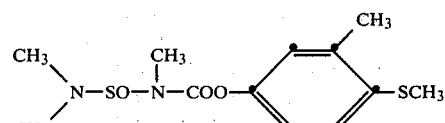

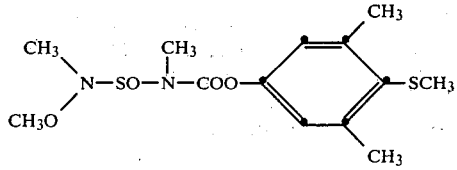

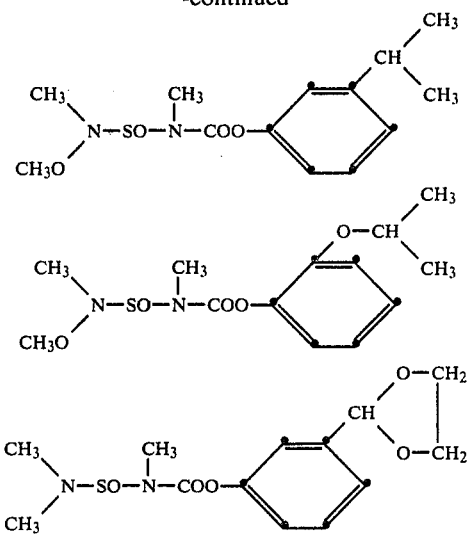

The compounds of the formula I can be produced by methods known per se, for example as follows:

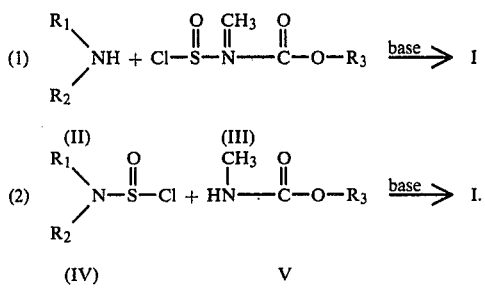

In the formulae II to V, the symbols $R_1$, $R_2$ and $R_3$ have the same meanings as defined under the formula I. Suitable bases for the processes 1 and 2 are: pyridine, alkylpyridines, such as picolines and lutidines, or tertiary amines such as trialkylamines, also hydroxides, oxides, carbonates and bicarbonates of alkali metals and alkaline-earth metals, as well as alkali metal alcoholates, for example potassium tert-butylate and sodium methylate.

The processes 1 and 2 are performed at a reaction temperature of between $-20°$ and $100°$ C., usually between $-10°$ and $50°$ C., under normal or elevated pressure, and preferably in an inert solvent or diluent. Suitable solvents or diluents are for example: ethers or ethereal compounds, such as diethyl ether, dipropyl ether, dioxane, dimethoxyethane and tetrahydrofuran; amides such as N,N-di-alkylated carboxylic acid amides; aliphatic, aromatic as well as halogenated hydrocarbons, especially benzene, toluene, xylenes, chloroform and chlorobenzene; nitriles such as acetonitrile; dimethyl sulfoxide, and ketones such as acetone and methyl ethyl ketone.

The starting materials of the formulae II to V are known or they can be produced by known methods.

The compounds of the formula I are suitable for combating various animal and vegetable pests, for example phytopathogenic nematodes.

The compounds of the formula I are particularly suitable however for combating insects, and phytopathogenic mites and ticks, for example of the orders: Lepidoptera, Coleoptera, Homoptera, Heteroptera, Diptera, Acarina, Thysanoptera, Orthoptera, Anoplura, Siphonaptera, Mallophaga, Thysanura, Isoptera, Psocoptera and Hymenoptera. The compounds of the formula I are above all suitable for combating insects that damage plants, especially insects that damage plants by eating, in crops of ornamental plants and productive plants, in particular in cotton crops (for example against Spodoptera littoralis and Heliothis virescens), and in vegetable crops (for example against Leptinotarsa decemlineata and Myzus persicae). Active substances of the formula I have a very favourable action also against flies, such as Musca domestica, and against mosquito larvae.

The acaricidal and insecticidal action can be substantially broadened and adapted to suit given circumstances by the addition of other insecticides and/or acaricides. Suitable additives are for example: organic phosphorus compounds, nitrophenols and derivatives thereof, formamidines, ureas, pyrethrin-like compounds, and also carbamates and chlorinated hydrocarbons.

Compounds of the formula I are combined particularly advantageously also with substances having a synergistic or intensifying effect. Examples of compounds of this type are, inter alia: piperonylbutoxide, propynyl ethers, propynyl oximes, propynyl carbamates and propynyl phosphonates, 2-(3,4-methylenedioxyphenoxy)-3,6,9-trioxaundecane (Sesamex or Sesoxane), S,S,S-tributylphosphorotrithioates and 1,2-methylenedioxy-4-(2-octylsulfinyl)-propyl)-benzene.

Compounds of the formula I can be used on their own or together with suitable carriers and/or additives. Suitable carriers and additives can be solid or liquid and they correspond to the substances common in formulation practice, such as natural or regenerated substances, solvents, dispersing agents, wetting agents, adhesives, thickeners, binders and/or fertilisers.

The compositions according to the invention are produced in a manner known per se by the intimate mixing and/or grinding of the active substances of the formula I with suitable carriers, optionally with the addition of dispersing agents or solvents which are inert to the active substances. The active substances can be obtained and used in the following forms:

solid preparations: dusts, scattering agents, granules (coated granules, impregnated granules and homogeneous granules);

liquid preparations:
(a) water-dispersible concentrates of active substance: wettable powders, pastes or emulsions;
(b) solutions.

The content of active substance in the compositions described above is between 0.1 and 95%; it is to be mentioned in this respect that with application from an aeroplane, or from other suitable devices, concentrations of up to 99.5% or even the pure active substance can be used.

The active substances of the formula I can be formulated for example as follows (parts are by weight).

Dusts

The following substances are used to produce (a) a 5% dust and (b) a 2% dust:
(a)
5 parts of active substance, and
95 parts of talcum; and
(b)
2 parts of active substance,
1 part of highly dispersed silicic acid, and
97 parts of talcum.

The active substance is mixed and ground with the carriers.

Granulate

The following ingredients are used to produce a 5% granulate:
5 parts of active substance,
0.25 part of epoxidised vegetable oil,
0.25 part of cetyl polyglycol ether,
3.50 parts of polyethylene glycol, and
91 parts of kaolin (particle size 0.3–0.8 mm).

The active substance is mixed with epoxidised vegetable oil and the mixture is dissolved in 6 parts of acetone; the polyethylene glycol and cetyl polyglycol ether are then added. The solution thus obtained is sprayed onto kaolin, and the acetone is subsequently evaporated off in vacuo.

Wettable powders

The following constituents are used to produce (a) a 40% wettable powder, (b) and (c) a 25% wettable powder and (d) a 10% wettable powder:
(a)
40 parts of active substance,
5 parts of sodium lignin sulfonate,
1 part of sodium dibutyl-naphthalene sulfonate, and
54 parts of silicic acid;
(b)
25 parts of active substance,
4.5 parts of calcium lignin sulfonate,
1.9 parts of Champagne chalk/hydroxyethyl cellulose mixture (1:1),
1.5 parts of sodium dibutyl-naphthalene sulfonate,
19.5 parts of silicic acid,
19.5 parts of Champagne chalk, and
28.1 parts of kaolin;
(c)
25 parts of active substance,
2.5 parts of isooctylphenoxy-polyoxyethylene-ethanol,
1.7 parts of Champagne chalk/hydroxyethyl cellulose mixture (1:1),
8.3 parts of sodium aluminium silicate,
16.5 parts of kieselguhr, and
46 parts of kaolin; and
(d)
10 parts of active substance,
3 parts of a mixture of the sodium salts of saturated fatty alcohol sulfates,
5 parts of naphthalenesulfonic acid/formaldehyde condensate, and
82 parts of kaolin.

The active substance is intimately mixed in suitable mixers with the additives, and the mixture is then ground in the appropriate mills and rollers to obtain wettable powders which can be diluted with water to give suspensions of the concentration desired.

Emulsifiable concentrates

The following substances are used to produce (a) a 10% emulsifiable concentrate, (b) a 25% emulsifiable concentrate and (c) a 50% emulsifiable concentrate:
(a)
10 parts of active substance,
3.4 parts of epoxidised vegetable oil, 3.4 parts of a combination emulsifier consisting of fatty alcohol polyglycol ether and alkylarylsulfonate calcium salt,
40 parts of dimethylformamide, and
43.2 parts of xylene;
(b)
25 parts of active substance,
2.5 parts of epoxidised vegetable oil,
10 parts of alkylarylsulfonate/fatty alcohol polyglycol ether mixture,
5 parts of dimethylformamide, and
57.5 parts of xylene; and
(c)
50 parts of active substance,
4.2 parts of tributylphenol-polyglycol ether,
5.8 parts of calcium-dodecylbenzenesulfonate,
20 parts of cyclohexanone, and
20 parts of xylene.

Emulsions of the required concentration can be prepared from these concentrates by dilution with water.

Sprays

The following constituents are used to produce (a) a 5% spray and (b) a 95% spray:
(a)
5 parts of active substance,
1 part of epoxidised vegetable oil, and
94 parts of ligroin (boiling limits 160°–190° C.); and
(b)
95 parts of active substance, and
5 parts of epoxidised vegetable oil.

The invention is further illustrated by the Examples which follow.

EXAMPLE 1

Production of the carbamate of the formula

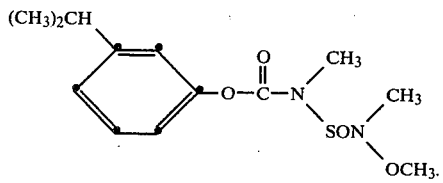

6.5 g of thionyl chloride are added dropwise at 0°–5° C. to a solution of 9.65 g of the compound of the formula

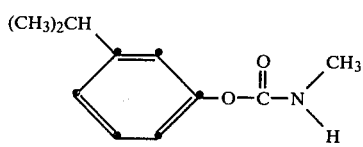

and 4.8 g of pyridine in 50 ml of tetrahydrofuran. After four hours' stirring at 20° C., there are slowly added dropwise firstly 4.8 g of pyridine, and then at 0°–5° C. 3.1 g of methoxymethylamine. The mixture is stirred for four hours at room temperature, and extracted twice with 50 ml of water each time. After drying, removal of the solvent by distillation, and purification by column-chromatography (SiO$_2$; chloroform), the product obtained is the compound of the formula

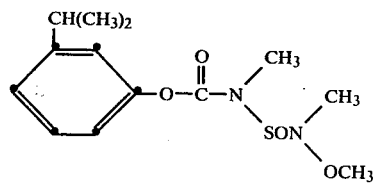

having a refractive index of $n_D^{20°} = 1.5184$.

The following compounds are produced in an analogous manner:

| | |
|---|---|
|  | $n_D^{20°} = 1,5155$ |
|  | $n_D^{20°}: 1,5150$ |
|  | $n_D^{20°}: 1,5131$ |
|  | $n_D^{20°}: 1,4902$ |
|  | $n_D^{20°}: 1,5287$ |
|  | $n_D^{20°}: 1,5750$ |
|  | $n_D^{20°}: 1,5486$ |

EXAMPLE 2: Insecticidal stomach-poison action: *Spodoptera littoralis, Dysdercus fasciatus* and *Heliothis virescens*

Cotton plants were sprayed with an aqueous emulsion containing 0.05% of the compound to be tested (obtained from a 10% emulsifiable concentrate). After drying of the coating, larvae of the species Spodoptera littoralis (L3 stage), Dysdercus fasciatus (L4) and Heliothis virescens (L3), respectively, were settled onto the plants. Two plants were used per test compound and per test species, and an assessment of the mortality rate obtained was made after 2, 4, 24 and 48 hours. The test was carried out at 24° C. with 60% relative humidity.

The compounds according to Example 1 exhibited in the above test a good action against larvae of the species Spodoptera littoralis, Dysdercus fasciatus and Heliothis virescens.

EXAMPLE 3: Insecticidal stomach-poison action: *Leptinotarsa decemlineata*

The test method described in Example 2 was repeated using larvae of the species Leptinotarsa decemlineata (L3), and potato plants instead of cotton plants, the procedure otherwise being the same.

The compounds according to Example 1 exhibited a good action against larvae of the species Leptinotarsa decemlineata.

EXAMPLE 4: Action against *Dermanyssus gallinae*

In each case, 50 Dermanyssus gallinae were immersed for a short time in an aqueous emulsion or solution containing 0.1, 1, 10 and 100 ppm, respectively, of the compound to be tested. The emulsions or solutions were then absorbed with cotton wool, and the wetted test insects were left in the contaminated test tubes. An assessment of the mortality rate achieved with each concentration was made after 3 days.

The compounds according to Example 1 exhibited in this test a good action against Dermanyssus gallinae.

EXAMPLE 5: Action against *Rhipicephalus bursa* (imagines and larvae), *Amblyomma hebraeum* (♀ imagines, nymphs and larvae) and *Boophilus microplus* (larvae-OP-sensitive and OP-tolerant)

The test objects used were larvae (in each case about 50), nymphs (in each case about 25) and imagines (in each case about 10) of *Rhipicephalus bursa, Amblyomma hebraeum* and *Boophilus microplus*. The test insects were immersed for a short time in an aqueous emulsion or solution containing 0.1, 1.0, 10, 50 and 100 ppm, respectively, of the compound to be tested. The emulsions or solutions in the test tubes were then absorbed with cotton wool, and the wetted test insects were left in the test tubes treated in this manner. An evaluation of the mortality rate achieved at each concentration was made after 3 days for larvae and after 14 days for nymphs and imagines.

The compounds according to Example 1 exhibited in this test a good action against larvae, nymphs and imagines of the species Rhipicephalus bursa and Amblyomma hebraeum as well as against larvae (OP-resistant and OP-sensitive) of the species Boophilus microplus.

EXAMPLE 6: Action against Musca domestica 50 g in each case of freshly prepared CSMA nutrient substrate for maggots were weighed off into beakers. A specific amount of a 1% (by wt.) aqueous formulation of the respective active substance (dispersible powder) was transferred by pipette to the nutrient substrate in each beaker. There were then deposited per active substance and concentration in each case 25 one-day-old maggots of *Musca domestica* in the respective beakers containing the nutrient substrate thus treated. After the maggots had pupated, the formed pupae were separated from the substrate by flushing with water, and placed into vessels closed with perforated lids. The pupae flushed out per group were counted (toxic effect of the active substance on the development of the pupae). The number of flies which had emerged from the pupae was then determined after 10 days.

The compounds according to Example 1 exhibited a good action in this test.

EXAMPLE 7: Action against *Aedes Aegypti*

Specific amounts of a 0.1% emulsion preparation of the active substance were transferred by pipette to the surface of 150 ml of water to obtain concentrations of 10, 5 and 1 ppm, respectively. Into each container were then placed 30–40 two-day-old Aëdes larvae. The mortality rate was determined after 1, 2 and 5 days.

The compounds according to Example 1 exhibited in this test a good action against *Aedes aegypti*.

EXAMPLE 8: Action against soil nematodes

In order to test their action against soil nematodes, the active substances were added at the respective concentration to soil infested with root-gall nematodes (Meloidogyne arenaria), and intimately mixed with the soil. In one test series, tomato seedlings were planted immediately after preparation of the soil, and in another test series tomatoes were sown after a waiting time of 8 days. In order to assess the nematocidal action, the galls present on the roots were counted 28 days after planting and sowing, respectively.

The active substances according to Example 1 exhibited in this test a good action against *Meloidogyne arenaria*.

What is claimed is:
1. A compound of the formula

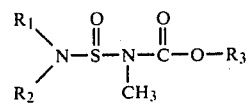

wherein
$R_1$ is hydrogen or $C_1$–$C_6$-alkyl,
$R_2$ is $C_1$–$C_6$-alkyl or $C_1$–$C_6$-alkoxy, and
$R_3$ is phenyl which is unsubstituted or mono- or polysubstituted by identical or different substituents selected from the group consisting of halogen, $C_1$–$C_6$-alkyl, $C_1$–$C_6$-alkoxy, $C_1$–$C_6$-alkylthio, $C_2$–$C_6$-alkenyl, $C_2$–$C_6$-alkynyl, nitro,

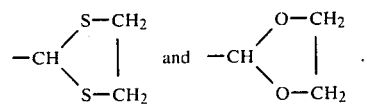

2. A compound according to claim 1, wherein $R_1$ is methyl $R_2$ is methyl or methoxy, and $R_3$ is phenyl which is mono- to trisubstituted by $C_1$–$C_6$-alkyl, $C_1$–$C_6$-alkoxy, $C_1$–$C_6$-alkylthio or

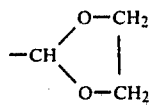

3. The compound according to claim 2 of the formula

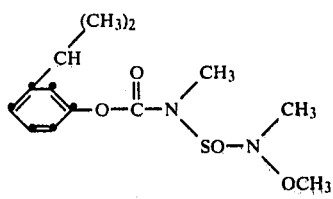

4. The compound according to claim 2 of the formula

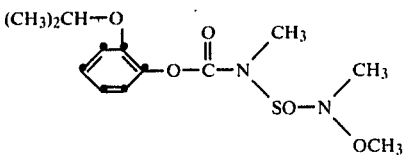

5. An insecticidal composition which comprises an insecticidally effective amount of a compound according to claim 1 as active ingredient, and suitable carriers and/or other additives.

6. A method for combating insects and acarides which comprises applying thereto, or to a locus infested with said insects or acarides, an insecticidally or acaricidally effective amount of a compound according to claim 1.

* * * * *